US012773528B2

(12) United States Patent
Meah

(10) Patent No.: US 12,773,528 B2
(45) Date of Patent: Oct. 27, 2026

(54) FLEXIBLE ASPIRATION SYSTEM

(71) Applicant: Maaz Meah, Glen Ellyn, IL (US)

(72) Inventor: Maaz Meah, Glen Ellyn, IL (US)

(*) Notice: Subject to any disclaimer, the term of this patent is extended or adjusted under 35 U.S.C. 154(b) by 279 days.

(21) Appl. No.: 16/359,423

(22) Filed: Mar. 20, 2019

(65) Prior Publication Data

US 2019/0290885 A1 Sep. 26, 2019

Related U.S. Application Data

(60) Provisional application No. 62/645,845, filed on Mar. 21, 2018.

(51) Int. Cl.

| | |
|---|---|
| ***A61M 25/00*** | (2006.01) |
| ***A61B 5/00*** | (2006.01) |
| ***A61B 10/02*** | (2006.01) |
| ***A61B 10/04*** | (2006.01) |

(52) U.S. Cl.

CPC ....... *A61M 25/0084* (2013.01); *A61B 5/6848* (2013.01); *A61B 10/0283* (2013.01); *A61B 10/04* (2013.01); *A61B 2010/045* (2013.01)

(58) Field of Classification Search

CPC .. A61M 2025/0091; A61M 2025/0089; A61M 25/0084; A61M 25/01; A61M 25/065; A61M 2025/0166; A61B 5/6848; A61B 5/02158; A61B 10/0283; A61B 10/04; A61B 2010/045; A61B 5/01; A61B 5/0215; A61B 2562/063

See application file for complete search history.

(56) References Cited

U.S. PATENT DOCUMENTS

| | | | | |
|---|---|---|---|---|
| 3,918,456 A * | 11/1975 | Patel | A61M 25/0014 | 604/104 |
| 4,222,380 A * | 9/1980 | Terayama | A61M 25/0084 | 604/164.01 |
| 4,857,057 A * | 8/1989 | Sanagi | A61M 37/00 | 604/170.01 |
| 5,147,311 A * | 9/1992 | Pickhard | A61M 5/148 | 604/153 |
| 5,162,044 A * | 11/1992 | Gahn | A61F 9/00745 | 606/128 |
| 5,593,385 A * | 1/1997 | Harrison | A61M 5/1412 | 604/83 |
| 5,964,740 A * | 10/1999 | Ouchi | A61M 25/0084 | 604/164.01 |
| 6,616,626 B2 * | 9/2003 | Crank | A61M 25/0108 | 604/48 |

(Continued)

FOREIGN PATENT DOCUMENTS

JP 3614943 B2 * 1/2005 ............. A61B 10/04

*Primary Examiner* — Cris L. Rodriguez

(74) *Attorney, Agent, or Firm* — Rocklaw PLLC; Michael T. Fluhler

(57) ABSTRACT

A flexible needle system may comprise a tubular body, a needle assembly and a connector body. The tubular body may include a leading end and a trailing end. The tubular body may be configured to flex between an initial configuration and a flexed configuration. The needle assembly may include a needle body with a needle extending therefrom. The leading end of the tubular body may be configured to selectively receive the needle body, and the trailing end of the tubular body may be configured to selectively receive the connector body. A method may include providing a flexible needle system.

20 Claims, 11 Drawing Sheets

(56) References Cited

U.S. PATENT DOCUMENTS

| | | | | |
|---|---|---|---|---|
| 7,549,424 | B2 * | 6/2009 | Desai | A61B 17/3403 606/14 |
| 10,154,798 | B2 * | 12/2018 | Greenburg | A61B 5/05 |
| 10,524,694 | B2 * | 1/2020 | Hunter | A61B 5/6885 |
| 2001/0023349 | A1 * | 9/2001 | VanTassel | A61P 43/00 606/53 |
| 2002/0082546 | A1 * | 6/2002 | Crank | A61M 25/0108 604/48 |
| 2007/0179455 | A1 * | 8/2007 | Geliebter | A61M 5/329 604/272 |
| 2010/0063478 | A1 * | 3/2010 | Selkee | A61M 25/0147 604/524 |
| 2012/0116248 | A1 * | 5/2012 | Mcweeney | A61B 10/0233 600/567 |
| 2012/0116376 | A1 * | 5/2012 | Hoey | A61B 18/04 606/27 |
| 2014/0171760 | A1 * | 6/2014 | Singh | A61M 25/0068 600/309 |
| 2015/0305770 | A1 * | 10/2015 | Fill | A61B 17/3478 600/235 |
| 2019/0142497 | A1 * | 5/2019 | Wegrzyn, III | A61B 18/1477 606/41 |
| 2025/0017469 | A1 * | 1/2025 | Barbagli | A61B 5/0036 |

* cited by examiner

FLEXIBLE ASPIRATION SYSTEM

CROSS-REFERENCE TO RELATED APPLICATION

This application is a non-provisional application that is based on and claims priority to U.S. Provisional Application No. 62/645,845 filed Mar. 21, 2018, which is incorporated by reference in its entirety.

BACKGROUND

Traditional aspiration techniques employ inflexible, visually obstructive and unsanitary structures. Typical instruments are positioned in a patient, but these instruments are inflexible and limit the access capabilities relative to curved or tortuous pathways therein. Further, typical instruments are non-transparent and thus obstruct visualization by surgeons. If the surgeon has limited direct or indirect visualization of the instrument, the trajectory of instrument within the anatomical structures of the patient may be unknown. Typical instruments also lack the ability for the surgeon to see materials flowing therethrough, or provide any indication of whether the procedure is complete. After use, traditional instruments are merely sterilized without any indication of whether biohazards still remain in the instrument and thus are prone to infection and spread of disease to the patient and others. There is a need for improved systems, devices and methods for optimized access, positioning, visualization, and sanitary practices.

BRIEF DESCRIPTION OF THE DRAWINGS

While the claims are not limited to a specific illustration, an appreciation of the various aspects is best gained through a discussion of various examples thereof. Referring now to the drawings, exemplary illustrations are shown in detail. Although the drawings represent the illustrations, the drawings are not necessarily to scale and certain features may be exaggerated to better illustrate and explain an innovative aspect of an example. Further, the exemplary illustrations described herein are not intended to be exhaustive or otherwise limiting or restricted to the precise form and configuration shown in the drawings and disclosed in the following detailed description. Exemplary illustrations are described in detail by referring to the drawings as follows:

DETAILED DESCRIPTION

Figure 1:
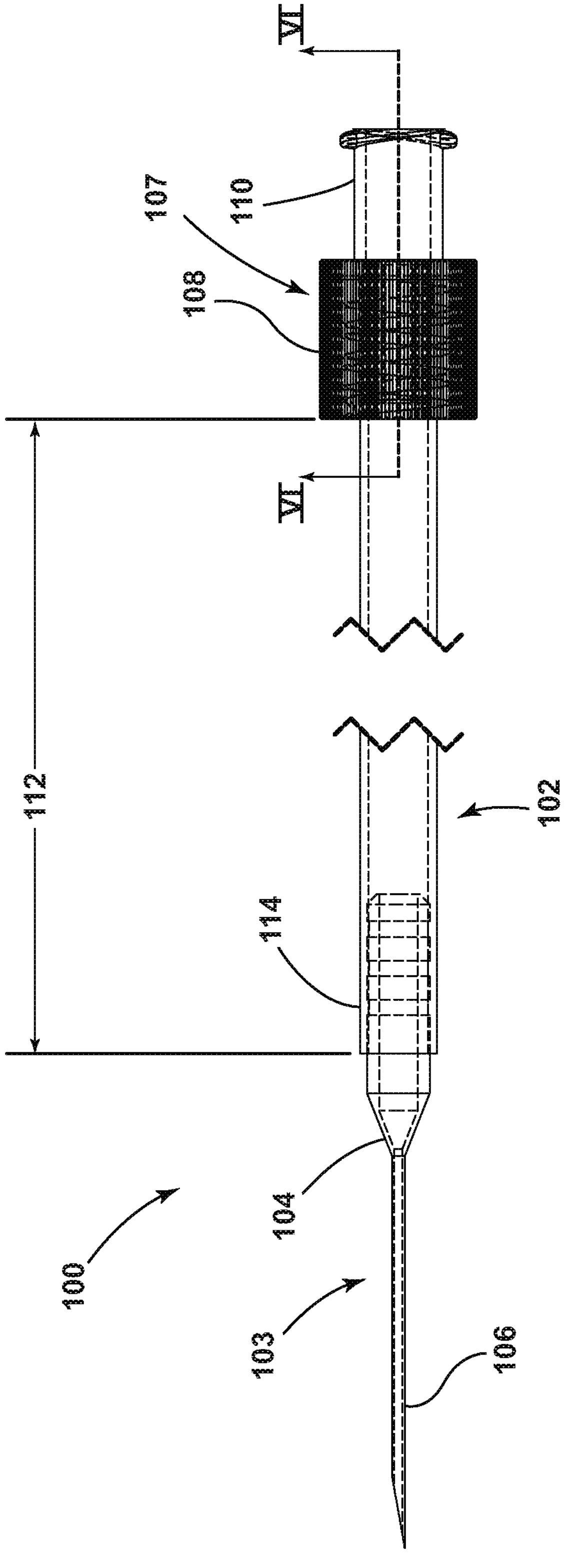
FIG. 1 illustrates a side view of an exemplary needle system of the present disclosure, e.g., in an initial configuration.
Figure 2:
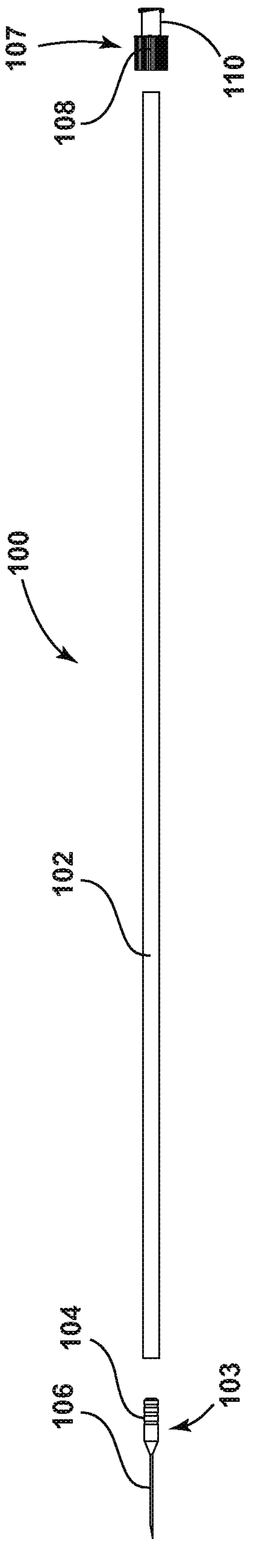
FIG. 2 illustrates an exploded view of the exemplary needle system of FIG. 1.
Figure 4:
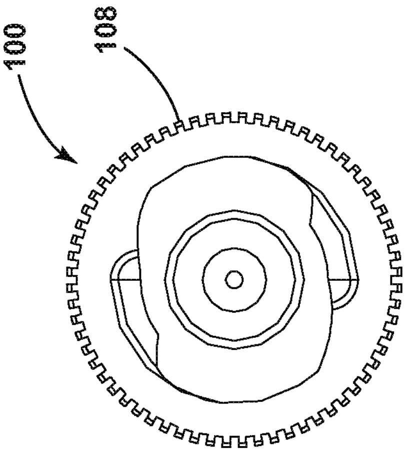
FIG. 4 illustrates a rear view of the exemplary needle system of FIG. 1.
Figure 3:
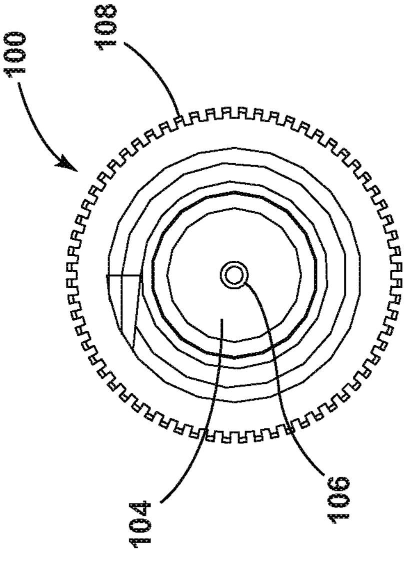
FIG. 3 illustrates a front view of the exemplary needle system of FIG. 1.
Figure 5:
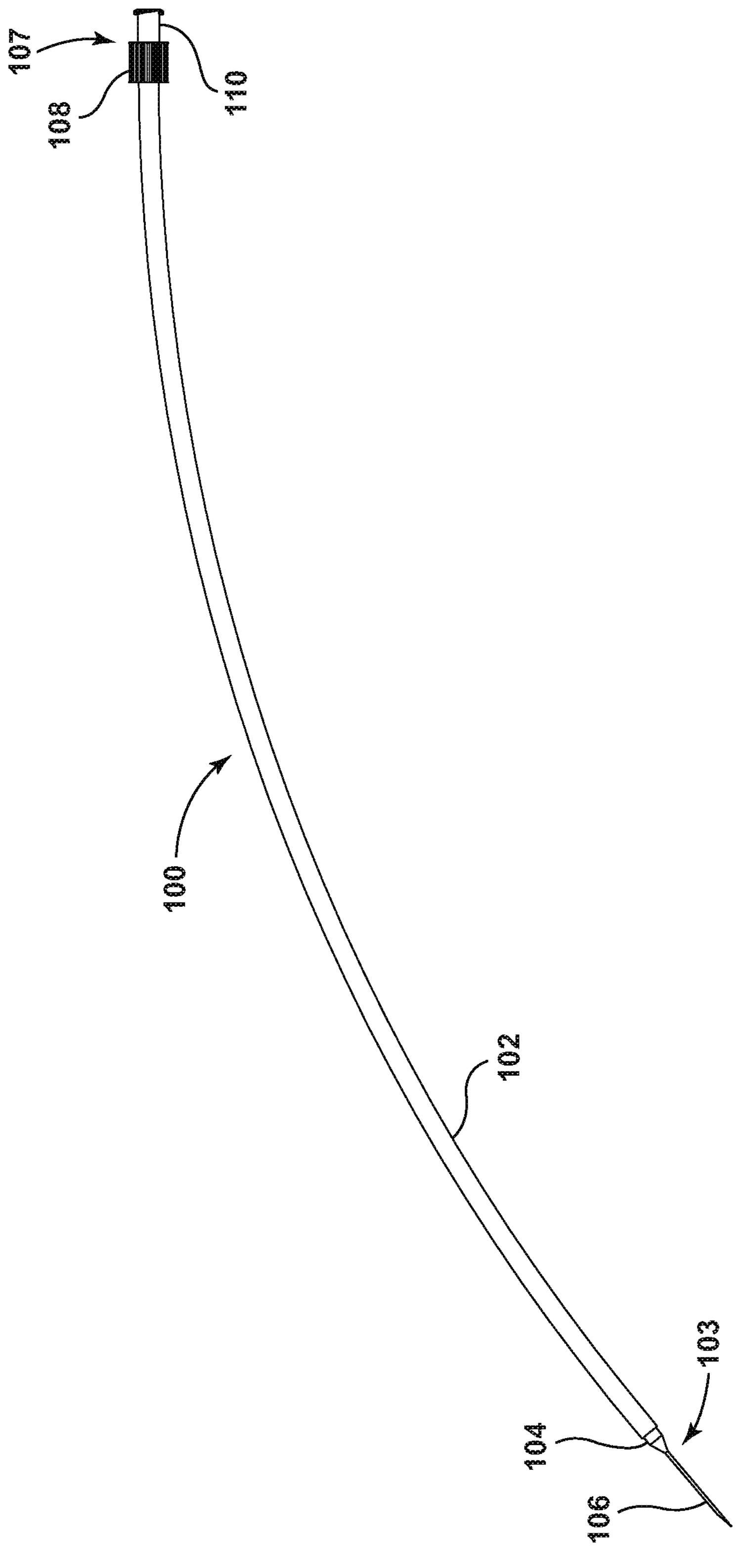
FIG. 5 illustrates another view of the exemplary system of FIG. 1 including, for example, a flexed configuration.

Embodiments of the present disclosure may employ more flexible, visually non-obstructive and sanitary structures. The present disclosure provides systems, devices and method for positioning aspiration systems for transfer of fluid with respect to a body opening of a patient, but with flexible and bendable structures to enhance access capabilities relative to curved or tortuous pathways through the anatomical structures within the patent. Further, embodiments may be transparent including semi-transparent and fully transparent so as to not obstruct and optimize visualization of the materials therein. Independently or in conjunction with direct or indirect visualization, embodiments may employ a plurality of sensors for providing sensor information with respect to the materials within and outside the system, and determining the sensor positions and trajectory relative to each other and surrounding anatomical structures of the patient. Moreover, embodiments may be configured for users to visualize or sensors to detect the consistency, flow rate, and type of materials flowing therethrough, or determine when appropriate materials have been removed from or injected into the patient. In addition, embodiments may include disposable or single use materials that may be disposed of along with contaminants thereby reducing infections and spread of disease. As a result, the systems, devices and methods herein are optimized for access, positioning, visualization, and sanitary practices.

A flexible needle system may comprise a tubular body, a needle assembly and a connector body. The system may be configured for any medical procedure for the aspiration, injection or withdrawal of any bodily, medical or other materials (e.g., fluids, tissues, or a combination thereof) with respect to a patient. The tubular body may include a leading end and a trailing end. The tubular body may be configured to flex between an initial configuration and a flexed configuration.

The needle assembly may include a needle body with a needle extending therefrom. The leading end of the tubular body may be configured to selectively receive the needle body, and the trailing end of the tubular body may be configured to selectively receive the connector body.

A tubular body may be configured to be bent between an initial configuration that is substantially straight and to a flexed configuration that is substantially curved. At least one of the tubular body, needle body and connecter body may include a substantially transparent material to view fluid therein. The tubular body may be configured to reduce bulging of the tubular body over the needle assembly. The leading end of the tubular body may be configured to selectively receive the needle body, and the trailing end of the tubular body may be configured to selectively receive the connector body.

All or any of the tubular body, needle assembly, and connector body may include an inner or outer surface having at least one of a luer taper, threaded (e.g., single, double or multi), press fit, mechanical interlock, rib-recess, adhesive, heated, melted, or bonded connection or a combination thereof relative to a corresponding inner or outer surface of each other or any other component herein. For example, at least one of the leading end and trailing end of the tubular body may include internal thread, external threads, or a combination thereof. The tubular body and the needle body may engage each other with at least one of a luer taper. The tubular body may be is received in the connection body, twisted relative to the connection body, and releasably secured thereto by way of a single, double or multi tooth thread.

Embodiments may include one or a plurality of sensors. The sensors may be along any of the tubular body, the needle assembly and connector body 103. The sensors may be positioned on or anywhere between a leading end and a trailing end of the tubular body, needle assembly, connector body 103, or a trocar with a straight or curved body positioned about and for receiving the tubular body and/or needle assembly therein. The sensors may be embedded in the tubular body, needle assembly, connector body, trocar or a combination thereof. The sensors may be positioned on an outer or inner surface of the tubular body, needle assembly, connector body 103, trocar or a combination thereof.

FIGS. 1-5 illustrate needle system 100. System 100 may include a flexible needle system configured to bend between an initial or substantially straight configuration (e.g. FIG. 1) and a flexed or substantially bent configuration (e.g., FIG. 5). System may include a tubular body 102, a needle assembly 103, and a connector body 107. All or any portion of system 100 may be configured to be rigid, semi-rigid, flexible, bendable, transparent and/or opaque. System 100 may be optimized for direct or indirect visualization, robotic surgery, and use of one or more sensors.

With reference to FIG. 1, the needle assembly 103 may be configured to penetrate skin of a patient and transfer fluid to the patient (e.g., inject fluid) or transfer fluid from the patient (e.g., withdraw fluid). The needle assembly 103 may include a needle body 104 with a needle 106 extending therefrom.

The tubular body 102 may be configured to provide fluid communication between the needle assembly 103 and the connector body 107. The tubular body 102 may include a flexible, bendable, semi-rigid, or rigid material, a transparent, semi-transparent, or opaque material, or combination thereof. The tubular body 102 may include leading end 114 configured to prevent or reduce bulging area 114 of the tubular body 102 over the needle assembly 103, e.g., by way of a rib-recess connection with the needle assembly 103. The tubular body 102 may include any working length 112.

Figure 6:
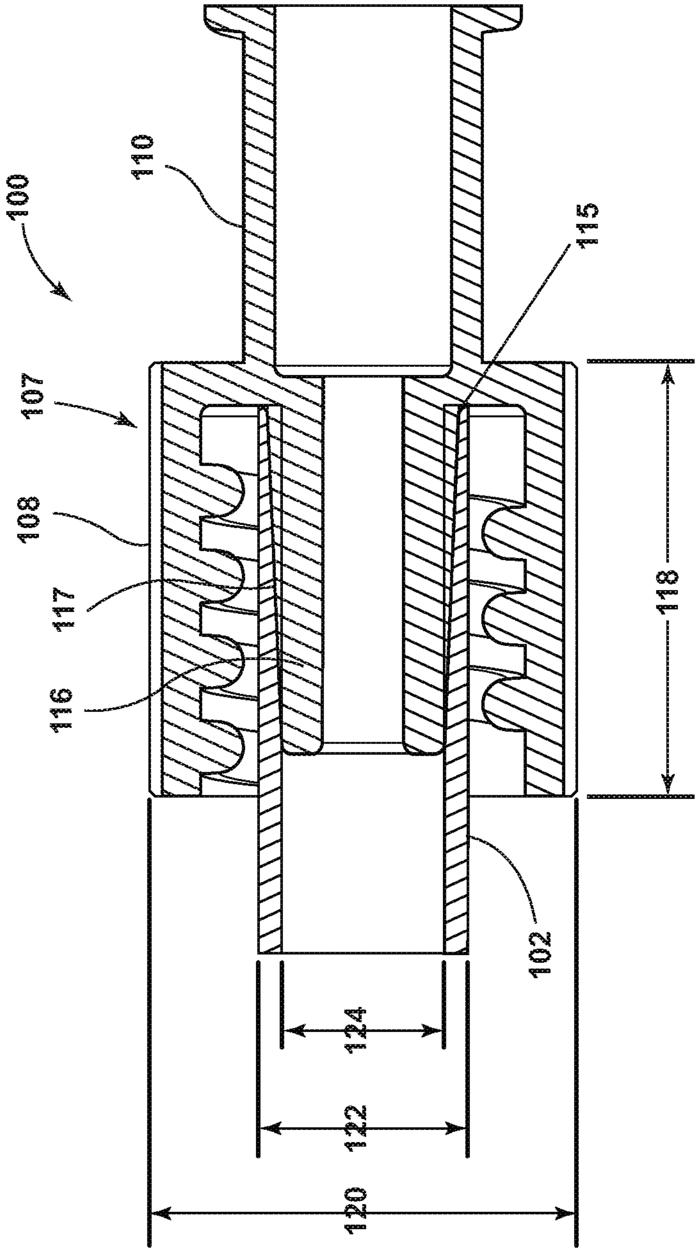
FIG. 6 illustrates a closer, cross section view of the exemplary needle system of FIG. 1.
Figure 7:
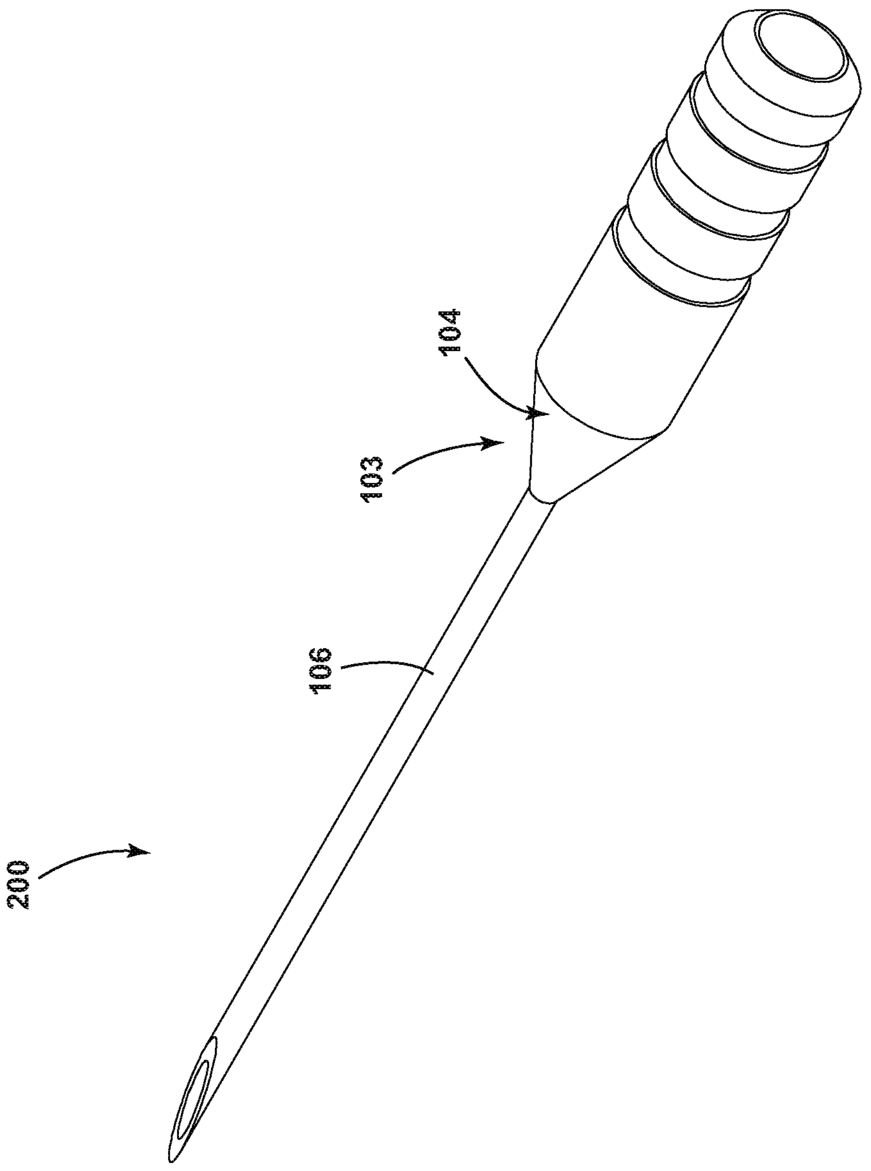
FIG. 7 illustrates an isometric view of a needle assembly of an exemplary needle system.
Figure 8:
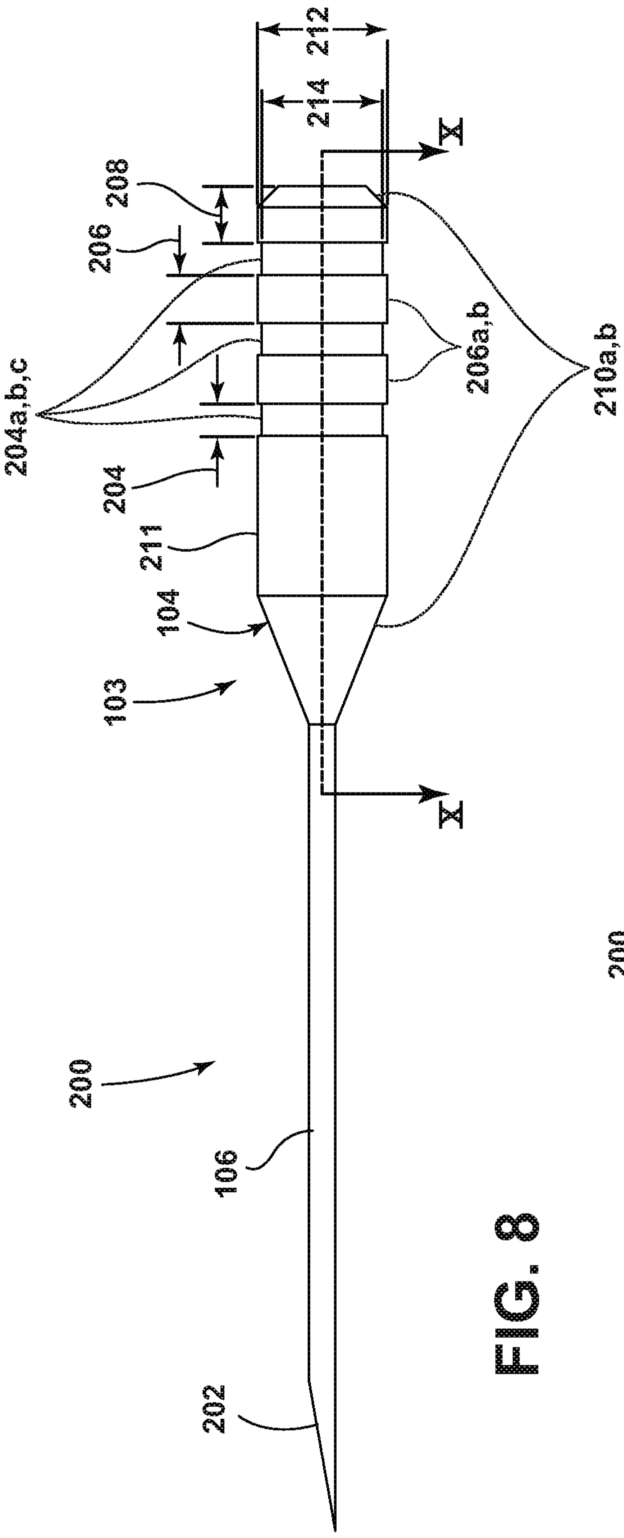
FIG. 8 illustrates a side view of the needle assembly of FIG. 7.
Figure 9:
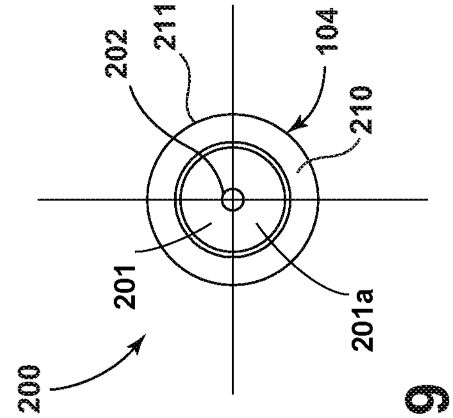
FIG. 9 illustrates a front view of the needle assembly of FIG. 7.

FIG. 6 illustrates the fluid connection between tubular body 102 and connector body 107. Tubular body 102 may include end face 115, an outer surface 122, and an inner surface 124. The connector body 107 may include a hub 108 having an outer hub surface 120 and a transverse hub surface 118. Hub 108 may include fitting 116 with taper 117 (e.g., luer type) configured to connect the hub 108 relative to the connector body 107, e.g., in combination with a threaded connection. The connector body 107 may include a connector 110 (e.g., a single, double or multi tooth thread) configured to connect to a corresponding connector of the cannula, catheter or tube.

FIGS. 7-10 illustrate assembly 200 including needle assembly 103. As shown in the isometric view of FIG. 7, needle assembly 103 may include needle 106 with needle tip 202 (e.g., beveled). With reference to the side view of FIG. 8, needle body 104 may include chamfer 210*a* (e.g., a leading chamfer), outer body surface 211, and a trailing chamfer 210*b*. Needle body 104 may include recesses 204, ridges 206 and end 208 with chamfer 210. Ridges 206 may include a ridge surface 212, and recesses 204 may include a recess surface 214. Recesses 204 may be in an alternating arrangement of a plurality of recesses and ridges, e.g., a first recess 204*a*, a first ridge 206*a*, a second recess 204*b*, a second ridge 206*b*, and a third recess 204*c*. The recesses 204 and/or ridges 206 may have constant, varying, increasing, decreasing, or staggered outer diameters. As shown in the front or leading end view of FIG. 9, needle assembly 103 may include needle tip 202, chamfer 201 (e.g., leading chamfer 201*a*), and outer body surface 211.

Figure 10:
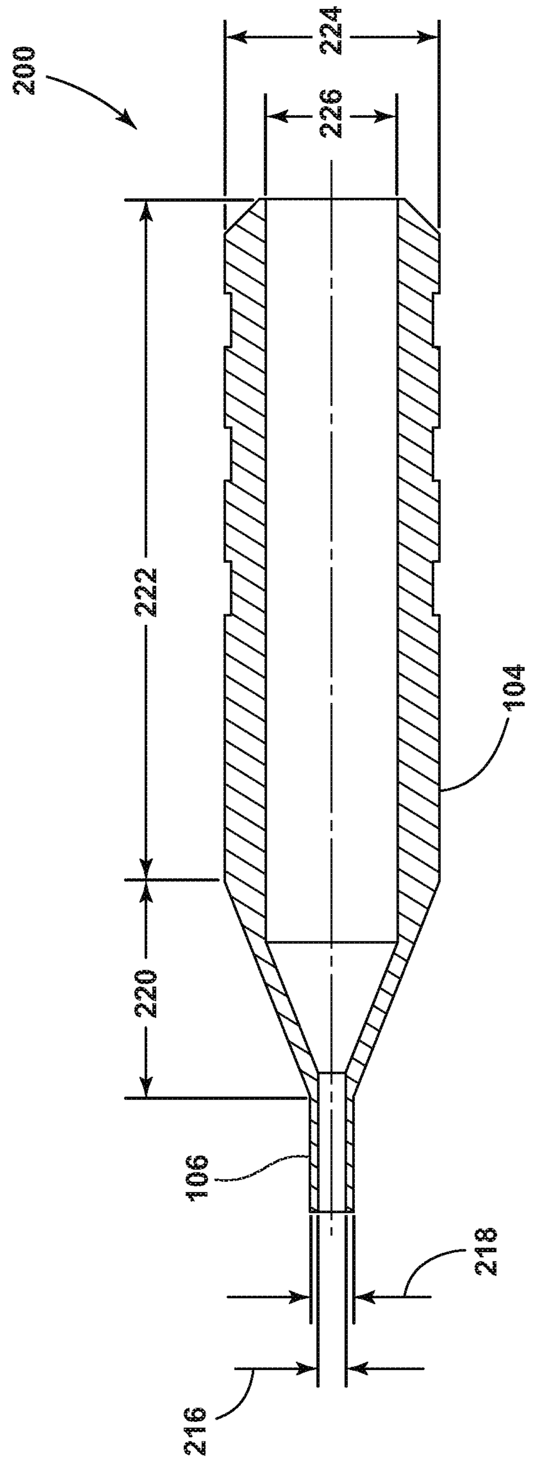
FIG. 10 illustrates a cross section view of the needle assembly of FIG. 7.
Figure 11:
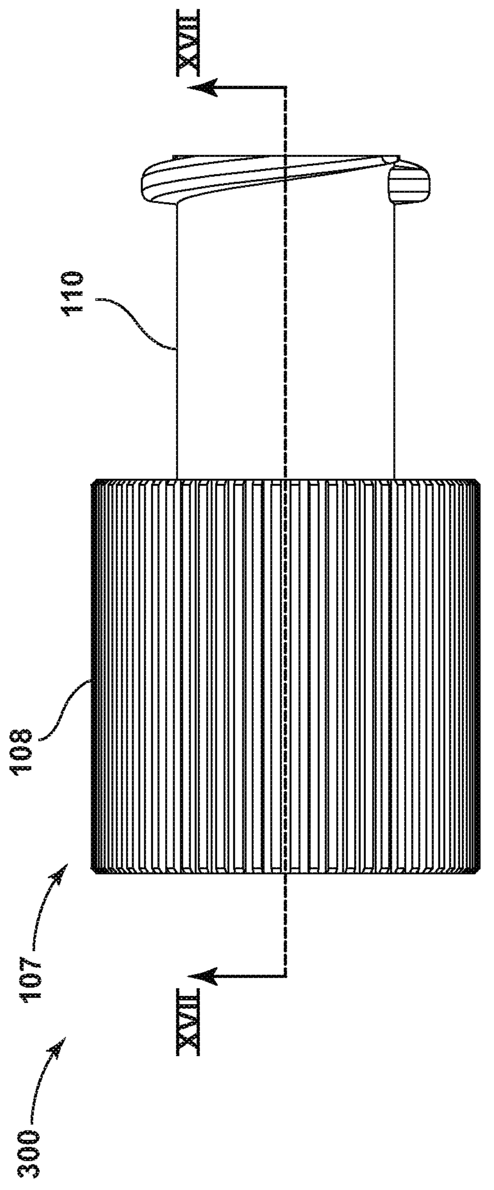
FIG. 11 illustrates a side view of a connector body of an exemplary needle system.
Figure 12:
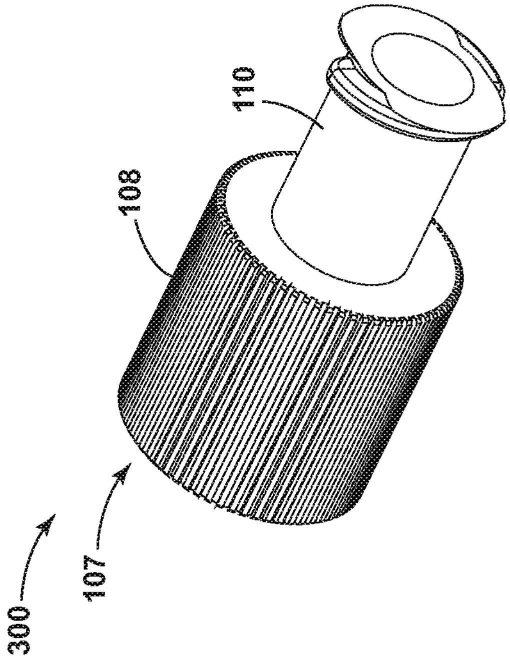
FIG. 12 illustrates a front isometric view of the rear connection assembly.

FIG. 10 illustrates a cross section view of assembly 200. Needle 106 may include an outer surface 218 and an inner surface 216. Needle body 104 may include tapered portion 220, rib-recess portion 222, outer surface 224, and inner surface 226. Outer surface 224 may be configured to be positioned in a portion of needle body 104. Alternatively, inner surface 226 may be configured to receive a portion of needle body 104.

FIGS. 11-17 illustrate assembly 300 including connector body 107. A shown in the side view of FIG. 11, connector body 107 may include hub 108 and connector 110. Hub 108 may include an outer surface that tapers inward or outward relative connector 110 and that includes a plurality of circumferential grips or ridges in an axial direction. Connector 110 may include a proximal end extending from hub 108 and a distal end having one or more external spiral protrusions or threads configured to engage an inner surface of tubular body 102. Hub 108 may include internal locking features configured to engage tubing in fluid communication with a positive or negative pressure source.

Figure 13:
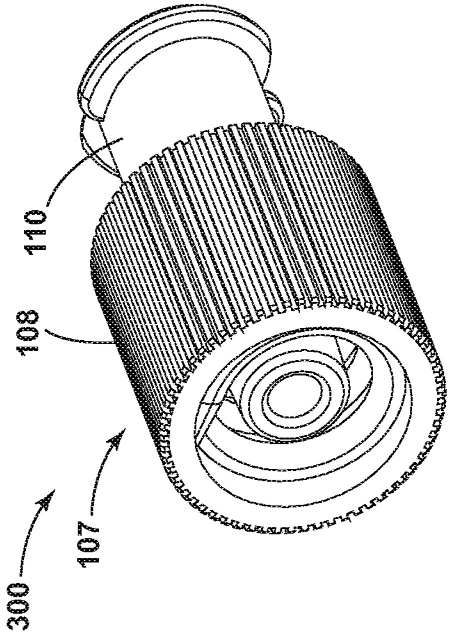
FIG. 13 illustrates a rear isometric view of the rear connection assembly.
Figure 14:
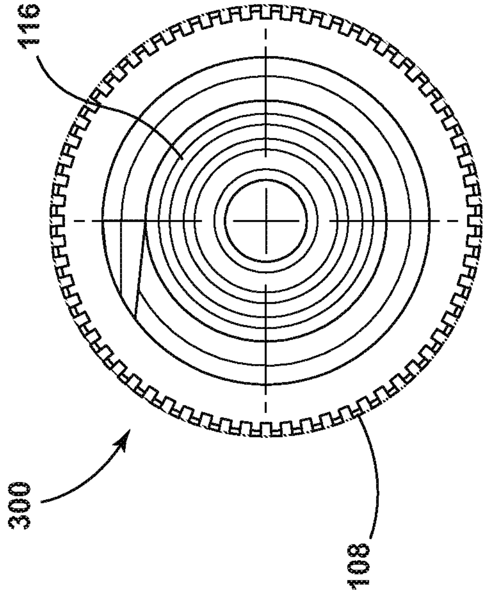
FIG. 14 illustrates a front view of the rear connection assembly.
Figure 15:
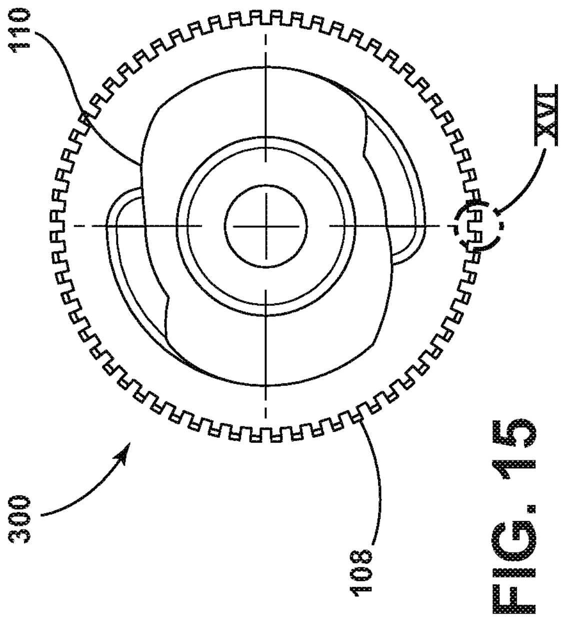
FIG. 15 illustrates a rear view of the rear connection assembly.
Figure 16:
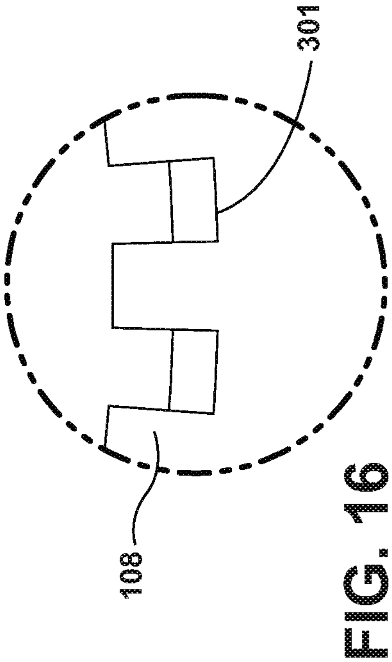
FIG. 16 illustrates a closer view of FIG. 15.

As shown in FIGS. 12-16, connector 110 may include external spiral protrusions or threads (e.g., FIGS. 12 and 15) and hub 108 may include internal locking features (e.g., FIGS. 13 and 14). As shown in FIG. 16, the internal locking features of hub 108 may include a textured, channeled or geared surface 301 to improve grip of hub 108, e.g., for turning and connecting connector body 107 relative to tubular body 102.

Figure 17:
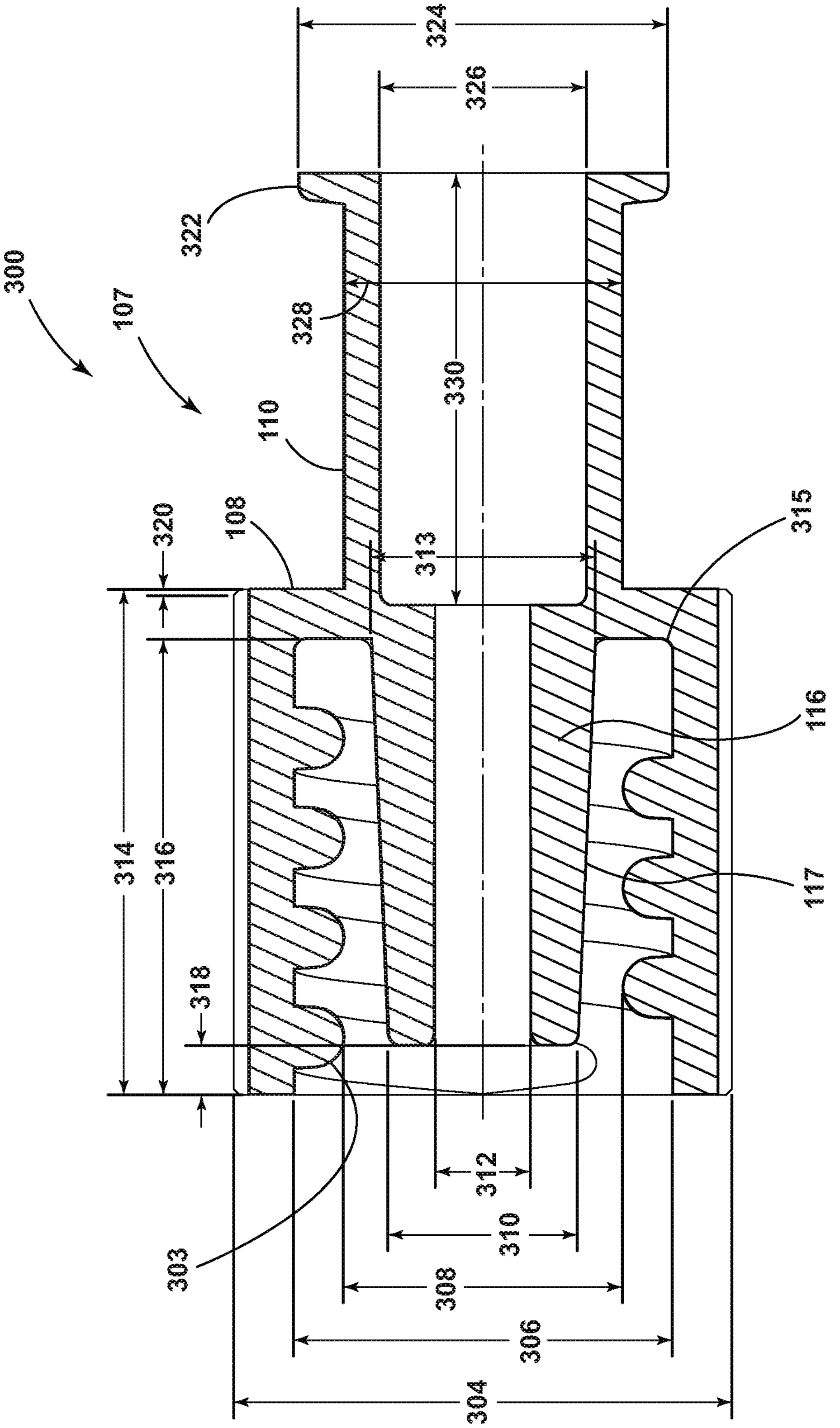
FIG. 17 illustrates a cross section view of the rear connection assembly.

As shown in FIG. 17, hub 108 of connector body 107 may include any outer surface 304. Hub 108 may include threaded connection 303 (e.g., internal) having an outer threaded surface 306 and an inner threaded surface 308. Fitting 116 may include inner surface 312 and outer surface 310 with taper 117 (e.g., luer type) extending to fitting base 313. Hub 108 may include rounds 315 between outer threaded surface 306, outer surface 310, thread depth 316, or a combination thereof. Hub 108 may include any length 314, thread depth 316, and fitting offset depth 318. One or both ends of hub 108 may include chamfer 320. Connector 110 of connector body 107 may include thread 322, e.g., single, double or multi tooth thread. Connector 110 may include outer thread surface 324, inner connector surface 326, outer connector surface 328, and cavity 330.

Figure 18:
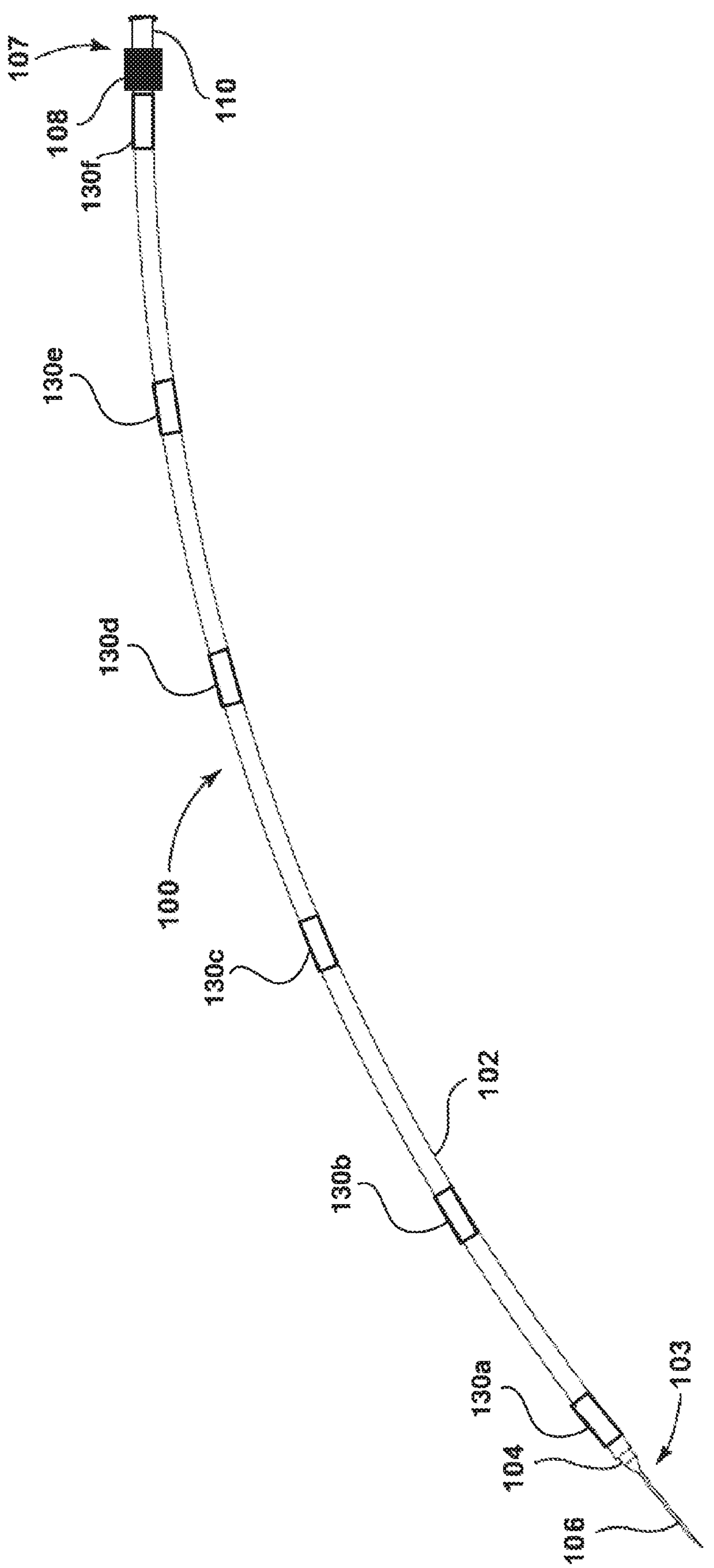
FIG. 18 illustrates another exemplary needle system of the present disclosure.

With reference to FIG. 18, needle system 100 may include one or a plurality of sensors 130*a-f*, tubular body 102, needle assembly 103 and connector body 107. The tubular body 102 may be configured to flex between an initial configuration and a flexed configuration. The needle assembly may include needle body 104 with a needle 106 extending therefrom. The leading end of the tubular body 102 may be configured to selectively receive the needle body 104, and the trailing end of the tubular body may be configured to selectively receive the connector body 107.

The sensors 130 may be along any of the tubular body 102, needle assembly 103 and connector body 103. The sensors 130 may be positioned on or anywhere between a leading end and a trailing end of the tubular body 102, needle assembly 103, connector body 103, or a trocar with a straight or curved body positioned about and for receiving the tubular body 102 and/or needle assembly 103 therein. The sensors 130 may be embedded in the tubular body 102, needle assembly 103, connector body 103, trocar or a combination thereof. The sensors 130 may be positioned on an outer or inner surface of the tubular body 102, needle assembly 103, connector body 103, trocar or a combination thereof.

Sensors 130 may be operatively connected to each other. The sensors 130 may be in wired or wireless communication with each other, one or more user interface devices having a processor for performing operations on the sensor information, memory to store the sensor information and a display to display the sensor output, or a combination thereof. Sensors 130 may be configured to generate sensor information including at least one of flow rate, material type, material density, material translucence, material inductance, vibration, pressure, and temperature. One or the plurality of sensors 130 may include a flow rate sensor, pressure sensor, proximity sensor, photoelectric sensor, optical sensor, piezoelectric sensor, transducer, electrostatic sensor, and thermocouple configured to generate the sensor information. The sensors 103 may be configured to determine the relative position or trajectory of any of sensors 130*a-f* relative to any one of the other sensors 130*a-f* or anatomical structures within the patient.

The sensor information generated by sensors 130 may be based on the relative or aggregate sensor information of sensors 103*a-f* of materials inside or outside of the system 100. The sensor information may be based on fluid (e.g., blood, body tissue or medicine) in or flowing through system 100. The sensor information may be based on fluid or structures outside the system 100. The sensor information may be based on fluid that is at least one of inside and outside the tubular body. The sensor information may be based on body tissue that is at least one of inside and outside the tubular body.

A method of a flexible needle system may comprise providing a tubular body, a needle assembly and a connector body. The tubular body may include a leading end and a trailing end. The tubular body may be configured to flex between an initial configuration and a flexed configuration. The needle assembly may include a needle body with a needle extending therefrom. The leading end of the tubular body may be configured to selectively receive the needle body, and the trailing end of the tubular body may be configured to selectively receive the connector body.

It will be appreciated that the aforementioned method and devices may be modified to have some components and steps removed, or may have additional components and steps added, all of which are deemed to be within the spirit of the present disclosure. None of the components or steps herein are essential elements nor is their interdependency required. Even though the present disclosure has been described in detail with reference to specific embodiments, it will be appreciated that the various modifications and changes can be made to these embodiments without departing from the scope of the present disclosure as set forth in the claims. The specification and the drawings are to be regarded as an illustrative thought instead of merely restrictive thought.

What is claimed is:

1. A flexible needle system for anatomical structures of a patient, the system comprising:

a tubular body having a leading end and a trailing end, the tubular body being configured to flex between an initial configuration and a flexed configuration;

a plurality of sensors extending inline along a longitudinal axis of the tubular body from the leading end to the trailing end, each of the plurality of sensors being in communication with each other to determine respective sensor positions and a trajectory relative to one another and the anatomical structures, and the plurality of sensors being operatively connected to each other such that at least two of the plurality of sensors are configured to generate sensor information including at least one of flow rate, material type, material density, material translucence, material inductance, and vibration;

a needle assembly including a needle body having a proximal end with an outer body surface positioned in the leading end of the tubular body and a distal end with a needle extending therefrom; and a connector body, wherein the leading end of the tubular body is configured to selectively receive the needle body, and the trailing end of the tubular body is configured to selectively receive the connector body.

2. The system of claim 1, wherein the plurality of sensors is at least one of embedded in the tubular body, on an outer surface of the tubular body, or on an inner surface of the tubular body.

3. The system of claim 1, wherein at least one of the plurality of sensors includes at least one of a flow rate sensor, proximity sensor, photoelectric sensor, optical sensor, piezoelectric sensor, transducer, electrostatic sensor, and thermocouple configured to generate the sensor information.

4. The system of claim 1, wherein the sensor information is based on fluid that is at least one of inside and outside the tubular body.

5. The system of claim 1, wherein the tubular body is configured to be bent from the initial configuration that is substantially straight and to the flexed configuration that is substantially curved.

6. The system of claim 1, wherein the needle body is a substantially transparent material to view fluid therein.

7. The system of claim 1, wherein the tubular body is configured to reduce bulging of the tubular body over the needle assembly.

8. The system of claim 1, wherein the leading end of the tubular body is configured to selectively receive the needle body, and the trailing end of the tubular body is configured to selectively receive the connector body.

9. The system of claim 1, wherein the tubular body is received in the connection body, twisted relative to the connection body, and releasably secured by at least one of a luer taper, threaded, press fit, mechanical interlock, rib-recess, adhesive, heated, melted, and bonded connection.

10. The system of claim 1, wherein the leading end of the tubular body includes threads.

11. The system of claim 1, wherein the tubular body and the needle body engage each other with at least one of a luer taper, threaded, press fit, mechanical interlock, rib-recess, adhesive, heated, melted, and bonded connection.

12. The system of claim 1, wherein the tubular body and the connector body engage each other with at least one of a luer taper, threaded, press fit, mechanical interlock, rib-recess, adhesive, heated, melted, and bonded connection.

13. The system of claim 1, wherein the needle body includes a transparent needle body, the plurality of sensors extending along the transparent needle body to generate the respective sensor positions and the trajectory relative to the initial and flexed configurations.

14. A flexible needle system for anatomical structures of a patient, the system comprising:

a tubular body having a leading end and a trailing end, the tubular body being configured to flex between an initial configuration and a flexed configuration;

a plurality of sensors extending inline along a longitudinal axis of the tubular body from the leading end to the trailing end, each of the plurality of sensors being in communication with each other to determine relative sensor positions and a trajectory relative to one another and the anatomical structures, and the plurality of sensors being operatively connected to each other such that at least two of the plurality of sensors are configured to generate sensor information including at least one of flow rate, material type, material density, material translucence, material inductance, and vibration; and a needle assembly including a needle body with a needle extending therefrom;

wherein the tubular body is configured to receive a plurality of sensors axially spaced along the tubular body, and wherein the leading end of the tubular body is configured to selectively receive the needle body.

15. The system of claim 14, wherein the plurality of sensors is at least one of embedded in the tubular body, on an outer surface of the tubular body, and on an inner surface of the tubular body.

16. The system of claim 14, wherein the tubular body is configured to be bent from the initial configuration that is substantially straight and to the flexed configuration that is substantially curved.

17. The system of claim 14, wherein needle body is a substantially transparent material to view fluid therein.

18. The system of claim 14, wherein the plurality of sensors wherein the needle body includes a transparent needle body, the plurality of sensors extending along the transparent needle body to generate the respective sensor positions and the trajectory relative to the initial and flexed configurations.

19. A method of a flexible needle system, comprising:

providing a tubular body having a leading end and a trailing end, the tubular body being configured to flex between an initial configuration and a flexed configuration;

providing a needle assembly including a transparent needle body configured to flex between the initial and flexed configurations of the tubular body and having a needle extending therefrom;

providing a connector body adapted to the tubular body, wherein the leading end of the tubular body is configured to selectively receive the needle body, and the trailing end of the tubular body is configured to selectively receive the connector body; and providing a plurality of sensors extending inline along a longitudinal axis of the tubular body from the leading end to the trailing end, the plurality of sensors being operatively connected to each other such that at least two of the plurality of sensors are configured to generate sensor information including at least one of flow rate, material type, material density, material translucence, material inductance, and vibration.

20. The method of claim 19, the plurality of sensors extending along the transparent needle body to generate the respective sensor positions and the trajectory relative to the initial and flexed configurations.

* * * * *